United States Patent [19]

Mansson

[11] 4,126,048
[45] Nov. 21, 1978

[54] ULTRASONIC PULSE TESTING APPARATUS WITH INTERFACE GATING

[75] Inventor: Sven E. Mansson, Hollviksnas, Sweden

[73] Assignee: Magnetic Analysis Corporation, Mount Vernon, N.Y.

[21] Appl. No.: 827,235

[22] Filed: Aug. 24, 1977

[51] Int. Cl.² ............................................. G01N 29/04
[52] U.S. Cl. ....................................................... 73/611
[58] Field of Search ................. 73/610, 611, 612, 614; 358/112

[56] References Cited

U.S. PATENT DOCUMENTS

| | | | |
|---|---|---|---|
| 2,682,766 | 7/1954 | Van Valkenburg | 73/611 |
| 3,262,306 | 7/1966 | Henry | 73/611 |
| 3,309,913 | 3/1967 | Weighart | 73/614 |
| 3,538,753 | 11/1970 | Gericke | 73/614 |
| 3,646,805 | 3/1972 | Walters | 73/611 |
| 3,733,891 | 5/1973 | Weighart | 73/614 |
| 3,972,228 | 8/1976 | Mansson | 73/614 |
| 4,033,177 | 7/1977 | Case | 73/611 |

Primary Examiner—Stephen A. Kreitman
Attorney, Agent, or Firm—Pennie & Edmonds

[57] ABSTRACT

An interface signal gate and received interface and flaw signals are displayed by a cathode-ray tube on respective sweeps from a first sweep generator having coinciding baselines. The gate as displayed is adjustable in height, width and position to enable the operator to select the desired interface signal. When adjusted so that the height of the interface signal exceeds the gate height, a trigger signal is produced which controls a second sweep generator to display flaw signals occurring after the interface signal. Sweeps from the second generator are displaced from the sweeps of the first generator, as displayed, and alternately display received signals and a flaw signal gate which is adjustable in height, width and position to select flaw signals above an adjustable threshold level for indication, etc. Received signals and interface and flaw signal gates are continually displayed on predetermined sweeps from the two sweep generators. A first sweep and interface gate are produced by each transmitted pulse, and a second sweep and flaw signal gate are produced by each trigger signal, and respective sweeps and gates and the received signals are blocked from the CRT during other than the predetermined sweeps during which the received signals and gates are respectively displayed. Echo checking is provided in which a sub-multiple of the PRF of the transmitted pulses is employed.

8 Claims, 8 Drawing Figures

ULTRASONIC PULSE TESTING APPARATUS WITH INTERFACE GATING

The present invention relates to ultrasonic non-destructive pulse testing apparatus and particularly to such apparatus with improved interface gating.

Ultrasonic non-destructive pulse testing apparatus is known in which an ultrasonic transducer is pulse driven to apply ultrasonic pulses to an object to be tested, and received signals corresponding to variations or defects in the object are displayed on a cathode-ray tube (CRT) and used to actuate indicating apparatus such as an alarm, marker, recorder, etc. Commonly the received signals are echoes reflected back from the front and rear surfaces of the object, and from flaws, defects, discontinuities or other variations in the object between front and rear surfaces.

A single ultrasonic transducer is often used for transmission and reception, although separate transducers may be employed. To facilitate applying the ultrasonic pulses to the object and receiving signals therefrom, a couplant such as water, oil, etc. is usually introduced between the transducer(s) and the object under test. Relative movement between transducer(s) and object may be used to scan various portions of the object.

Depending on test conditions and the shape of the object, the distance from the transducer to the object may be small or large, and may vary as the object moves. Thus it is frequently desired to start the display of signals with the first interface signal (from the front surface of the object) so that the operator can concentrate his attention on only those signals produced by variations or defects in the object itself (hereinafter collectively termed flaw signals), and so that indicating apparatus can be similarly confined.

The display of received signals including interface signals may be rather complicated and confused. In addition to front and rear surface interface echoes and flaw echoes from the object itself, there may be large echoes from the bottom of the tank in which the object is placed, and multipath echoes may exist which seemingly are between the transmitted pulse and the front surface of the object. Considerable noise may be present. The echo pattern may also change as the object is moved through the test zone not only because of changing echoes from the object itself but also because the propagation velocity will commonly be different in the object and in the couplant liquid so that the observed positions of echoes such as those from the bottom of the tank will appear to change as relative distances in the object and couplant change.

Accordingly it is considered important to enable the operator to select from the complete received signal display the appropriate interface echo for producing an expanded sweep showing the signals occurring after the interface. Advantageously both the complete and expanded sweeps are continually displayed so that the operator can note changes in the overall signal pattern and make readjustments as required, and can be continually assured that the proper interface signal is actually being used.

In accordance with the present invention first and second sweep generators are employed for supplying sweeps to cathode-ray tube means for displaying received signals including interface and flaw signals. An adjustable interface gate generator synchronized with the first sweep generator produces an interface signal gate at a selectable position along the sweeps. An adjustable threshold circuit is supplied with received signals and with the interface signal gate and produces trigger signals when received signals within the gate exceed the threshold level. Means connected with the threshold circuit produces from the interface signal gate a display interface signal gate having an amplitude substantially equal to the minimum amplitude of received signals as displayed which will actuate the threshold circuit to produce trigger signals. The display interface signal gate and received signals are displayed during different sweeps from the first sweep generator having coinciding baselines. Thus the operator can readily adjust the interface gate position to bracket the desired interface signal, as observed on the CRT display, and adjust the threshold level so that the interface signal exceeds the observed amplitude of the interface gate, and the proper trigger signals will be produced. Advantageously the width of the interface signal gate is adjustable so that the operator can exclude echo signals near the interface signal which might cause false actuation of the trigger circuit.

The trigger signals control the initiation of sweeps produced by the second sweep generator, thus producing expanded sweeps on which signals occurring after the interface are displayed. A flaw signal gate generator synchronized with the second sweep generator produces a flaw signal gate. An adjustable flaw threshold circuit supplied with received signals and with the flaw signal gate produces output signals when received signals within the flaw gate exceed an adjustable threshold level, and the output signals actuate indicator circuits such as an alarm, recorder, etc. Advantageously the flaw signal gate and received signals are displayed during different sweeps from the second sweep generator having coinciding baselines, and the baselines of sweeps from the second sweep generator are displaced from the baselines of sweeps from the first sweep generator. Thus the operator can readily note any changes in the first sweeps and readjust the interface gate if necessary.

Preferably the flaw signal gate as displayed on the second sweeps has an amplitude equal to the minimum amplitude of received signals as displayed on the second sweeps which will produce the output signals, and is adjustable in width and position, as described in my U.S. Pat. No. 3,972,228, issued Aug. 3, 1976.

In the specific embodiment described hereinafter the first sweep generator and the interface gate generator produce a sweep and a gate respectively upon the occurrence of each transmitted pulse, and the second sweep generator and the flaw signal gate generator produce a sweep and a gate respectively upon the occurrence of each trigger signal. Respective sweeps and gates and the received signals are blocked from the CRT during other than the predetermined sweeps during which they are respectively displayed. Thus a trigger signal is produced during each sweep interval once the interface gate has been adjusted, and a flaw output signal is produced during each sweep interval once the flaw gate has been adjusted, even though the received signals and the gate are displayed during different sweeps.

A high transmitting PRF (Pulse Recurrence Frequency) is often desired to facilitate rapid testing. In such case echoes produced by one pulse may be received after the next pulse has been transmitted, and may be erroneously identified as interface echoes or flaw echoes. Echo checking means are provided in which predetermined transmitter pulses are eliminated to yield a PRF which is a sub-multiple of the PRF being used for testing, while maintaining unchanged the slope of the sweeps from the first sweep generator and the time occurrence of the sweeps with respect to the non-eliminated pulses. If echoes obtained at the normal PRF disappear at the sub-multiple PRF, or are markedly reduced in amplitude, erroneous identification is indicated and the gate positions may be readjusted, or the PRF lowered.

Further features of the invention will be understood from the following description of a specific embodiment thereof.

DESCRIPTION OF THE SPECIFIC EMBODIMENT

Figures 1, 3:
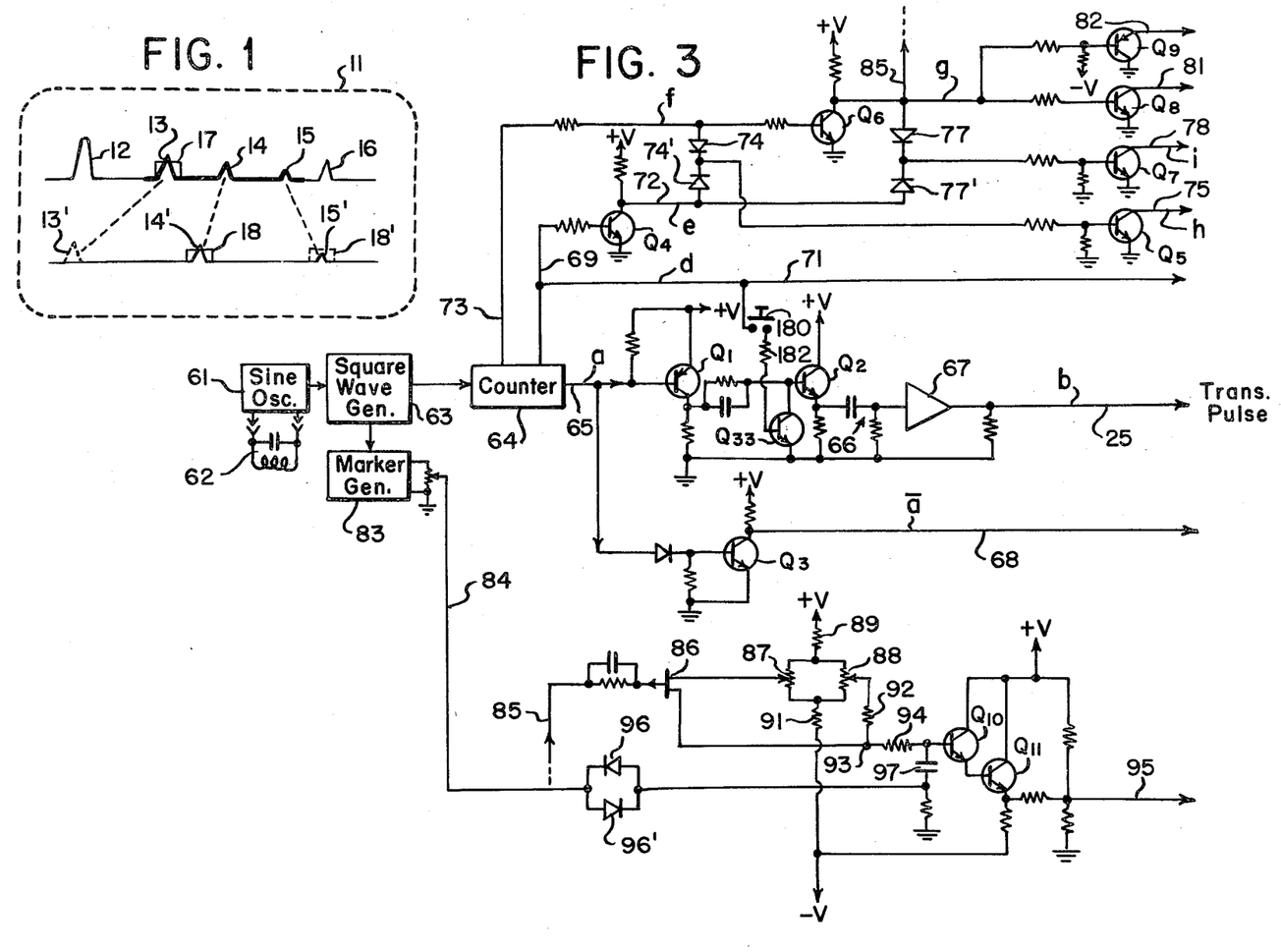
FIG. 1 is an illustrative oscilloscope display.
FIG. 3 is a schematic of the transmitter pulse and blocking wave generators.

Referring to FIG. 1, the face of a cathode-ray tube oscilloscope is indicated by the dash line 11. The upper display comprises two sweeps having the same baseline. One sweep displays the complete received video signal including the transmitter pulse 12, the front surface or first interface echo signal 13 of an object under test, echo signals 14, 15 from flaws in the object, and a second interface echo signal 16. The second sweep displays an interface signal gate 17 of adjustable position, height and width.

The lower display likewise comprises two sweeps having the same baseline, and is vertically displaced from the upper display by a desired amount. One sweep displays a portion of the upper video signal display beginning with the first interface signal 13' and subsequent flaw signals 14', 15' on an expanded scale. The second sweep displays a flaw signal gate 18 of adjustable position, height and width.

In operation, an operator can move the upper interface gate 17 along the upper video display to select the first interface echo signal 13 and adjust the height and width of the gate so that only the desired signal exceeds the height of the gate. When this is done, the coincidence of the signal 13 within the gate 17 initiates the sweeps of the lower display so that only echo signals from beyond the first interface appear on the lower trace. The operator may then move the flaw gate 18 along the lower display and adjust its height and width so that only echo signals within the gate and exceeding the gate height actuate flaw indicator circuits such as a recorder, marker, alarm, etc. Thus, with gate 18 positioned as shown in full lines, echo signal 14' will be selected for indication. On the other hand, if the gate is moved to the dotted position 18', echo signal 15' will not be indicated since its height is less than the gate height. The gate height could be reduced to select 15' for indication.

The sweeps of either the upper or lower displays, or both, can be expanded as desired to display only the regions of interest. Also, if desired, the gate 17 on the upper display could be used to select some other echo signal for initiating the sweeps of the lower display.

Figure 2:
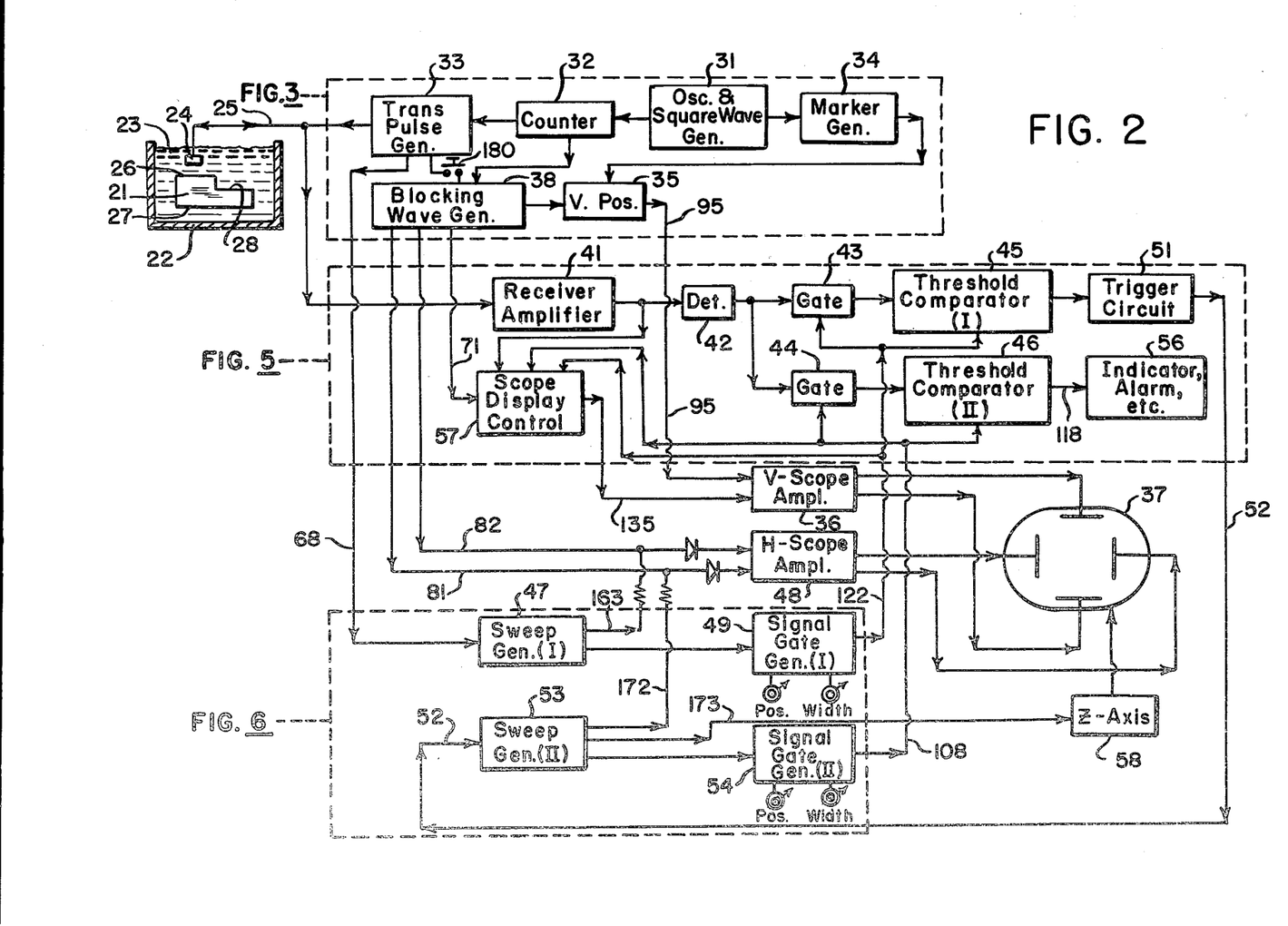
FIG. 2 is a block diagram of apparatus in accordance with the invention.

FIG. 2 shows a block diagram of the overall apparatus. Many transducer test arrangements are known for applying ultrasonic pulses to an object and picking up echoes therefrom, with which the present invention can be used. A single transducer can be used to both transmit pulses to the object and receive echoes therefrom, or separate transducers can be employed. Commonly a liquid such as water, oil, etc. is used as a coupling medium between a transducer and the object under test. In FIG. 2 a simple arrangement is shown for illustrative purposes in which the object 21 under test is placed in a tank 22 containing water 23. An ultrasonic transducer 24 receives driving pulses through line 25 and produces corresponding ultrasonic pulses directed toward object 21. An ultrasonic pulse produces a first interface echo at the upper (first) surface 26 of the object, such as shown at 13 in FIG. 1. Discontinuities in the object will produce echoes such as shown at 14 and 15. When the applied pulse reaches the lower (second) surface 27, a second interface echo will be produced, such as shown at 16. A further echo may be produced when the applied pulse reaches the bottom of the tank. This is not shown in FIG. 1, although it could be displayed by using a sweep of longer time duration. The echoes are received by transducer 24 and converted to corresponding electrical (video) signals in line 25.

The length of time or delay between the transmitted pulse and the first interface echo will depend on the length of path in the water and the propagation properties, and will increase as the distance increases. For example, the delay would be greater if surface 28 were beneath the transducer. Irregularly shaped objects will give interface echoes of different delay as the object is moved beneath the transducer. Echoes from discontinuities within the object will have magnitudes varying with the size of the discontinuities, and the time delays will depend on their locations and the propagation properties of the object as well as the water path. Considerable noise may be present, particularly with highly sensitive apparatus. Also, echoes from the bottom of the tank may appear on a subsequent sweep, depending on the sweep duration, and multipath echoes may exist.

For these and other reasons, depending on the particular application, the video display may be rather complicated and confused. Thus it is highly desirable to enable the operator to select the appropriate echo signal on the upper display to trigger the lower display.

In FIG. 2, square waves from an oscillator and square wave generator 31 are supplied to a counter 32 and then to a transmitter pulse generator 33 whose output is supplied to line 25. Square waves from 31 are also supplied to a marker generator 34. The markers are supplied to a vertical position circuit 35 which controls the upper and lower levels of the displays of FIG. 1, and combined signals are supplied to the vertical deflection amplifier 36 of oscilloscope 37 (CRT). The oscilloscope is shown symbolically as having vertical and horizontal deflection plates.

Outputs of counter 32 are supplied to a blocking wave generator 38 whose outputs control the display of video signals and gates on proper sweeps of the CRT. It would be possible to use a double beam oscilloscope for producing the upper and lower displays of FIG. 1. However, a single beam oscilloscope is less expensive and is here used. Successive sweeps, in groups of four, are used to display in succession the upper video, interface gate, lower video and flaw gate. Different display orders could be used if desired. In general, in this embodiment the displays and sweeps are produced in regularly recurring sequence at the transmitter pulse frequency, and are blocked during the intervals they are not used for the CRT display.

Received signals from line 25, and the transmitter pulses from 33, are supplied to a receiver amplifier 41 and then to detector 42. The detector output is supplied to gates 43, 44 which are opened and closed by signals from gate generators 49 and 54. Detected signals passing through the gates are fed to respective threshold comparators 45, 46.

Pulses from the transmitter pulse generator 33 are supplied to sweep generator 47 which produces sweeps for the upper traces of FIG. 1. The sweeps are supplied to the horizontal deflection amplifier 48 of the oscilloscope, and are blocked out by waves from 38 during the lower trace displays. The sweeps are also supplied to signal gate generator 49 which produces an interface signal gate corresponding to that shown at 17 in FIG. 1. The signal gate is applied to gate 43 to pass the desired portion of the received signals to comparator 45. The signal gate from 49 is adjustable in position and width so that the operator can select the first interface echo signal (or other echo signal) as described before. The gated portion of the received signals is compared with an adjustable threshold in 45, and when an echo signal amplitude exceeds the threshold it acutates the trigger circuit 51 to supply a trigger pulse through line 52 to sweep generator 53 which produces sweeps for the lower displays of FIG. 1. The signal gate is also supplied to the scope display control circuit 57 and its amplitude as displayed is controlled to equal the minimum amplitude of received signals as displayed which will actuate the comparator to produce trigger signals.

Sweeps from 53 are supplied to gate generator 54 which produces a flaw signal gate corresponding to that shown at 18 in FIG. 1. The flaw signal gate is adjustable in position and width and is applied to gate 44 to pass the desired portion of the received signals to comparator 46. The threshold of the comparator is adjustable, and when a received echo signal exceeds the threshold a signal is supplied to indicator 56 which may be a recorder, marker, alarm, etc. The flaw signal gate is also supplied to scope display control 57 and its amplitude as displayed is made equal to the minimum amplitude of received signals as displayed which will actuate threshold comparator 46 to produce output signals to indicator 56.

Scope display control circuit 57 serves to display the proper signals on successive sweeps. It is supplied with echo signals from receiver 41, signal gates from generators 49 and 54 and blocking waves from 38, so that video and gate signals are fed to the vertical deflection amplifier 36 at the proper times for display.

In order to indicate to the operator just which portion of the received echoes on the upper display is being shown on the lower display, an output of sweep generator 53 is fed to a Z-axis control circuit 58 so as to brighten the portions of the upper display which correspond to the sweeps of the lower display.

FIG. 3 shows in more detail the portion of FIG. 2 within the upper dashed box. Small letters in FIG. 3 refer to corresponding waves in FIG. 4. Most of the transistors employed are of the NPN type with the emitter arrow pointing away from the base. Occasionally PNP types are employed with the emitter arrow pointing toward the base. Opposite types may be used if desired, with suitable change in voltage polarity.

An adjustable frequency sine wave oscillator 61 is tuned by switchable tank circuits, one of which is shown at 62. The sine wave is fed to a square wave generator 63 whose output has the same frequency as the sine wave. The square wave is fed to counter 64 which produces an output in line 65 at each selected number of cycles of the square wave. Various oscillator frequencies and counts may be employed as suits the intended application. In one embodiment selectable oscillator frequencies from 20 KHz to 1 MHz and a count of 20 have been employed.

Figure 4:
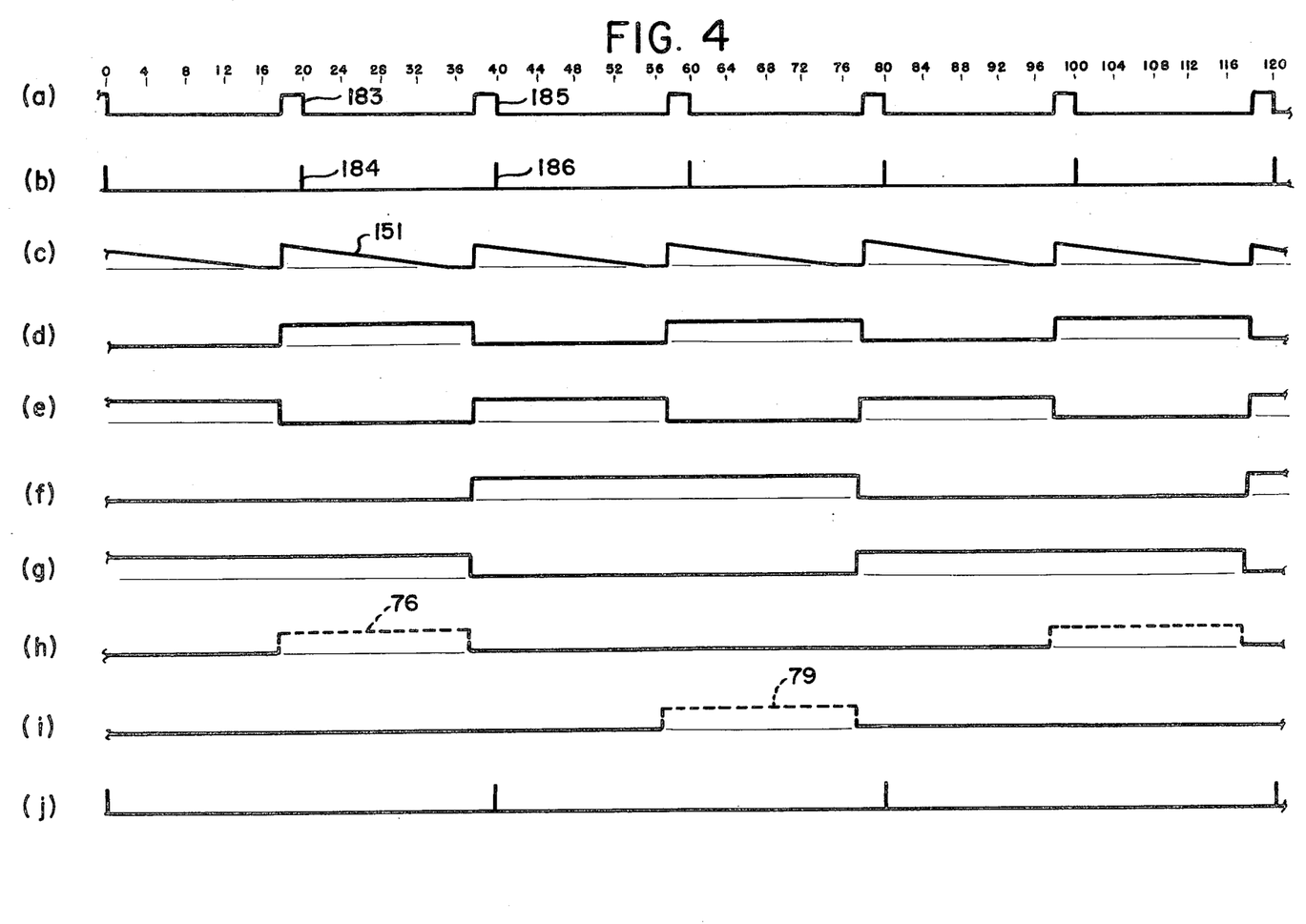
FIG. 4 shows waveforms for FIG. 3.

FIG. 4(a) shows the output in line 65. It goes high at a count of 18 and low at a count of 20, and repeats each 20 counts. The pulses are amplified in Q1 and supplied by emitter follower Q2 to an R-C differentiating circuit 66. The resultant short spikes are amplified in 67 and yield short transmitter pulses in output line 25 as shown at (b). These are applied to transducer 24 of FIG. 2. The pulses in line 65 are also applied to amplifier Q3 which produces inverted pulses denoted $\bar{a}$ in output line 68 for the sweep generator 47. Here and subsequently a bar over the designation of a waveform denotes the inverse waveform.

Counter 64 may be formed of commercially available units which produce various rectangular waves internally and combine them to yield desired waves, several of which are made available. Selected outputs are here used to produce the desired blocking waves.

A selected output in line 69 is shown in FIG. 4(d) and changes level each 20 counts, at the beginning of each pulse in (a). Accordingly, the output changes level successively for successive transmitter pulses, and is supplied to line 71. Line 71 connects to the oscilloscope display control of FIG. 2 and 5, and is used to alternately pass and block video signals on successive sweeps of the oscilloscope.

Line 69 is connected to inverter amplifier Q4 which yields waveform (e) in line 72. Another counter output in line 73 is selected having waveform (f), one-half the frequency of (d) or (e). Waveforms (e) and (f) are combined by back-to-back diodes 74,74' and Q5 which form an OR circuit yielding a low output (substantially ground) in line 75 when either input is high. When both inputs are low, line 75 is permitted to go high. The high output is shown dotted at 76 in FIG. 4(h) since its magnitude depends on the voltage applied to the collector of Q5, as will be described later.

Waveform (f) is inverted in Q6 to form (g). Waveforms (g) and (e) are combined by diodes 77, 77' and Q7 to yield a low output in line 78 when either input is high, and allowing line 78 to go high when both inputs are low, as shown dotted at 79 in FIG. 4(i).

Waveform (g) is applied to Q8 so that line 81 goes low when (g) is high, and is allowed to go high when (g) is low. The same waveform is applied to Q9 which is of opposite type (PNP) so that line 82 goes low when (g) goes low, and is allowed to go high when (g) goes high.

Each level of (g) lasts for two sweeps, and is used in a circuit for controlling the vertical positions of the upper and lower traces of FIG. 1. The output of Q6 in line 85 is supplied to the line bearing the same number at the bottom of FIG. 3, and through a coupling circuit to the gate of FET 86. FET 86 is on (conductive) when its gate potential is low and is off (non-conductive) when its gate potential is high.

Potentiometers 87 and 88 are connected in parallel and through resistors 89, 91 to positive and negative voltage sources which give the desired range of adjustment. The slider of 87, and the slider of 88 through resistor 92, are connected in the source-drain circuit of the FET. The junction point 93 connects through a resistor 94 to the base of Q10. Q10 and Q11 are connected as a cascade emitter follower and the output is supplied to line 95. When FET 86 is off, the voltage at 93 is primarily determined by the setting of potentiometer 88, and when the FET is on, primarily by potentiometer 87. Thus, the vertical positions of the upper and lower traces of FIG. 1 may be adjusted as desired, and the switching of FET 86 changes from upper to lower positions after two sweeps, and vice versa.

The square wave from generator 63 is supplied to marker generator 83 which includes a differentiating circuit to form sharp marker pulses of adjustable amplitude in output line 84. The resultant marker pulses are bottom clipped by the contact potentials of diodes 96, 96' poled in opposite directions and then supplied through coupling capacitor 97 to the base of Q10. Thus the markers appear in the output line 95 along with the vertical levels, and are supplied to the vertical scope amplifier 36 of FIG. 2. The corresponding amplifier output is applied to one of the vertical deflection plates. Advantageously the markers are applied to one vertical deflection plate and the video and gate signals to the other.

The waveforms in lines 81 and 82 are supplied to the horizontal amplifier 48 of FIG. 2 to block sweeps from generator 53 during the display of video and interface gates on the upper traces of FIG. 1, and to block sweeps from generator 47 during the display of video and flaw gates on the lower traces.

Figure 5:
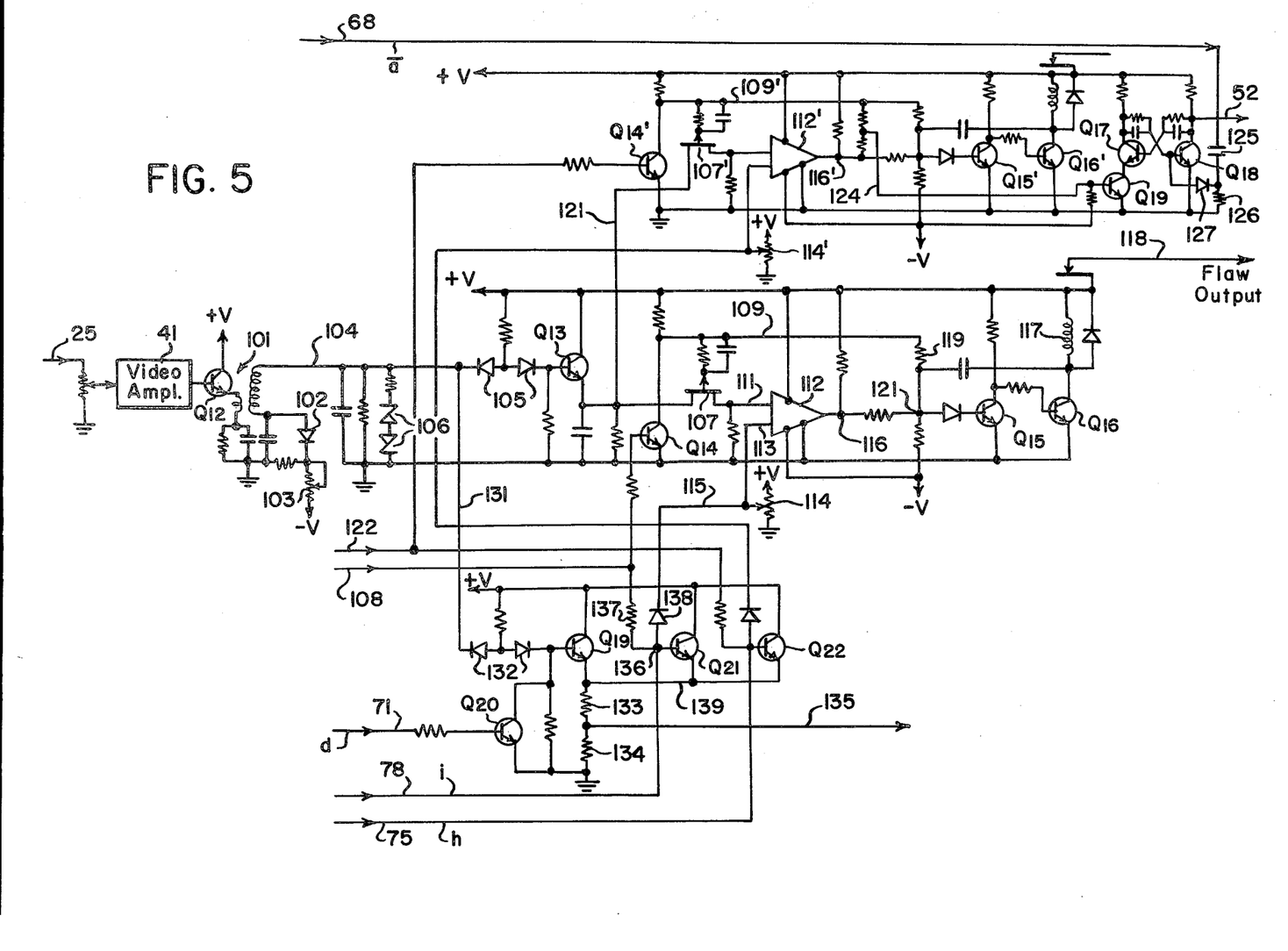
FIG. 5 is a schematic of the receiver, gated threshold circuits, and oscilloscope display control circuits.

Referring to FIG. 5, received signals in line 25 are applied through an adjustable attenuator to video amplifier 41. This may have autotransformer coupled emitter follower stages as described in the aforesaid patent. The output has been modified to allow adjusting the bias on the subsequent circuits. Transformer 101 has its primary in the emitter circuit of Q12 with an R-C biasing circuit to ground. The secondary is returned through diode 102 to a voltage divider connected to −V and including an adjustable resistor 103 for adjusting the bias so that the baseline of the video signals is the same as the baseline of the gate. The transformer output is supplied through line 104 and back-to-back diodes 105 to the base of detector Q13. Zeners 106 limit the amplitude of the transmitter pulses.

The echo signal output of Q13 is applied to a gating FET 107 controlled by Q14. A flaw signal gate corresponding to that shown at 18 on the lower display of FIG. 1 is supplied from line 108 to Q14 which is normally off and turned on by the signal gate. The gate of FET 107 is normally held high by the positive potential of line 109 and its source-drain circuit is non-conducting (off). When Q14 is turned on by a gating signal in line 108, FET 107 is turned on and the echo signals from Q13 are supplied to one input 111 of a comparator 112. An adjustable threshold voltage is applied to the other input 113 from potentiometer 114. The comparator amplifier 112 here shown normally has a positive output at point 116, and the output goes negative whenever an echo signal at input 111 equals or exceeds the threshold level at input 113. The signal at 116 is supplied through a diode to the base of Q15 which, with Q16, forms a one-shot multivibrator to lengthen the actuating echo and acutate relay coil 117. Normally Q15 is on and Q16 off. A negative echo signal at 116 cuts off Q15 and turns on Q16 to actuate the relay and thereby deliver a flaw output signal to line 118 which actuates an indicator 56 (FIG. 2).

To guard against possible false operation of the comparator by transients when the signal gate is off, line 109 is connected through resistor 119 to point 121 so that, in the absence of the gate signal, a negative output from the comparator at point 116 is insufficient to actuate the one-shot multivibrator. When line 109 goes low during a gate signal, the inhibition is removed.

Comparator 112 and the associated circuits for producing flaw signal outputs function as illustrated by the lower traces of FIG. 1. The upper portion of FIG. 5 shows a comparator arrangement which functions as illustrated by the upper traces of FIG. 1, and similar components are designated by the same numbers with an added prime. The detected signal from Q13 is supplied through line 121 to FET gate 107'. An interface signal gate corresponding to that shown at 17 in FIG. 1 is supplied from line 122 to Q14' to turn on FET 107' and supply the detected echo signals to comparator 112'. The comparator threshold is adjustable by potentiometer 114'. When an echo signal equals or exceeds the threshold, point 116' goes negative.

Certain changes in the upper comparator circuit will be described. As discussed before, an interface echo signal on the upper trace is selected by the operator and is used to trigger the lower traces. A one-shot multivibrator may react too slowly to generate the trigger signals. Accordingly, a high speed multivibrator circuit or flip-flop is used, comprising transistors Q17 and Q18, and is controlled by Q19. Q19 is normally on, by a positive bias applied to its base through line 124. Q17 is normally on and Q18 normally off, leaving output line 52 high. When the comparator output at 116' goes negative in response to the selected interface echo, the corresponding negative signal in line 124 turns off Q19. This turns off Q17 and Q18 is turned on to make output line 52 low. The negative going excursion is used to trigger the lower sweeps of FIG. 1, as will be explained later in connection with FIG. 6.

Upon termination of the interface echo, the comparator output at 116' goes positive, thereby turning on Q19 and reestablishing the emitter to ground circuit of Q17. Line 68 from FIG. 3 is connected to a differentiating circuit formed by capacitor 125 and resistor 126. Line 68 supplies waveform $\bar{a}$, the inverse of FIG. 4(a), which goes low before each transmitted pulse. The negative differentiated spike acts through diode 127 to cut off Q18, thereby quickly resetting the flip-flop, ready for the next interface echo.

In the operation here described, the one-shot multivibrator formed by Q15' and Q16' plays no part, and may be omitted. It is shown since, if interface gating is unnecessary for some applications, switching (not shown) may be provided to enable the upper comparator circuit to function as a flaw detector, similarly to the lower comparator circuit, thereby providing two flaw signal gates to select different echo signals for actuating an alarm, recorder, etc.

Comparators 112 and 112' both operate during each sweep interval under the control of respective gate pulses. Thus flaw signals and triggers for the lower sweeps are produced during successive sweep intervals. The echo signal and gate displays, however, take place successively as described above.

The switching of the displays for successive sweeps is produced by the circuit at the bottom of FIG. 5. The video signal in line 104 is supplied through line 131 and back-to-back diodes 132 to the base of Q19 which operates as an emitter follower. Emitter resistors 133, 134 form a voltage divider to deliver a desired fraction of the emitter voltage to output line 135. Q20 is connected across the input circuit of Q19. Blocking waveform d in line 71 (from FIG. 3) alternately turns Q20 off and on during alternate sweeps of the CRT, thereby delivering the video signal to the output line 135 every other sweep, and cutting it off in between. Line 135 is connected to the vertical CRT amplifier 36 in FIG. 2. Thus, echo signals are displayed during horizontal sweeps 1 and 3 of the CRT, but not during sweeps 2 and 4.

Q21 and Q22 control the interface and flaw signal gate displays on sweeps 2 and 4, respectively. Both are emitter followers sharing the same emitter resistors 133, 134 as Q19. Blocking waveform i from line 78 of FIG. 3 cuts off Q21 during sweeps 1, 2 and 3, but allows Q21 to be turned on during sweep 4, the flaw gate display sweep of the lower traces. Line 108 is normally low, and maintains Q21 off. During the flaw gate interval (18 in FIG. 1), line 108 goes high, thereby making point 136 high. Resistor 137 and diode 138 limit the positive voltage at 136 to the threshold voltage of line 115 plus the contact potential drop through diode 138.

As explained in the aforesaid patent, the height of the gate as displayed should equal the height of echo signals as displayed which will just reach the threshold level of the comparator. This requires taking into account contact potential drops in diodes and transistors through which the echo signals pass in the display and comparator circuits. Echo signals in line 131 encounter a contact potential drop between the base and emitter of Q19 in reaching the emitter line 139, and the base-emitter drop in Q13 in reaching comparator 112. The contact potentials of back-to-back diodes 105 and 132 cancel and need not be taken into account. The gate amplitude at point 136 encounters the base-emitter drop of Q21 in reaching line 139, and the drop of diode 138 in reaching the threshold line 115. Assuming transistors and diodes of the same material, say silicon, the base-emitter and diode drops are the same. Consequently, the relative amplitudes of echo and gate signals in line 139 correspond accurately to the relative amplitudes of echo signal and threshold voltage to the comparator.

Q22 is supplied with blocking wave h from line 75, and accordingly blocks the display of the interface signal gate from line 122 during sweeps 1, 3 and 4, but allows display during sweep 2. Q22 operates similarly to Q21, so that when the gate signal occurs during sweep 2 the relative amplitudes of echo and gate signals displayed on the upper traces accurately correspond to the relative amplitudes of the echo signals and threshold voltage at comparator 112'.

As will be understood, both echo and gate signals in line 139 will appear in line 135 with the same voltage division.

Figure 6:
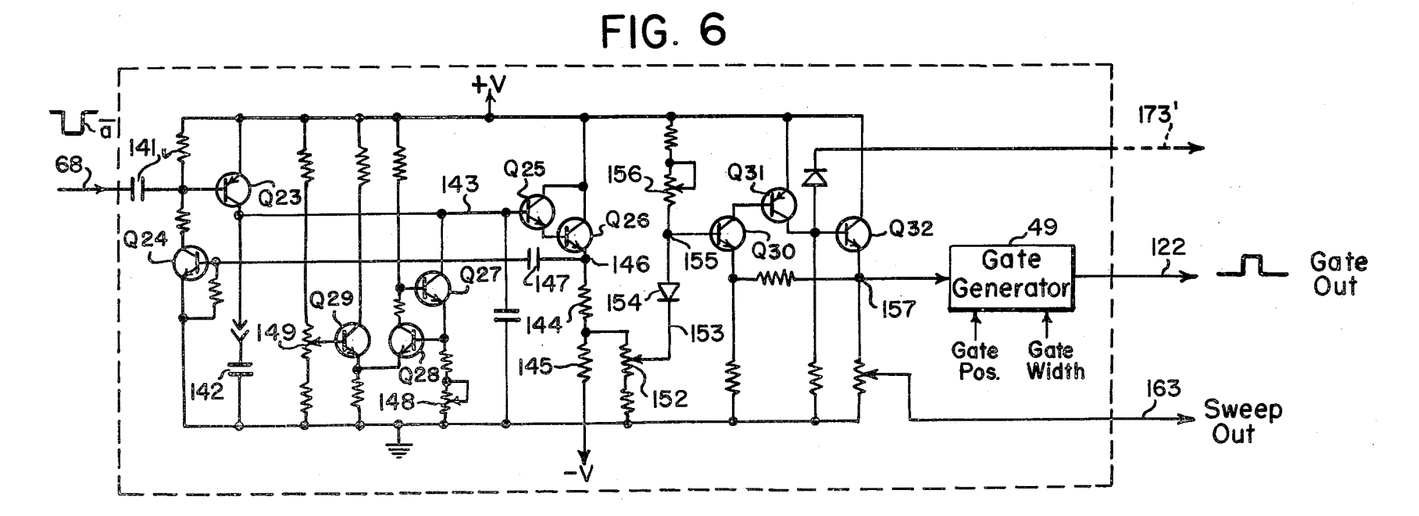
FIGS. 6 and 6(a) show sweep and gate generator circuits.

Referring to FIG. 6, a sweep generator is shown which operates similarly to that described in U.S. Pat. No. 3,972,228 although differing somewhat in detail. As shown, it generates sweeps for the upper traces.

Waveform $\bar{a}$ from line 68 of FIG. 3 is applied to a C-R differentiating circuit 141. Transistor Q23 is normally off, and is triggered on by the negative spike from the leading edge of $\bar{a}$. This charges the ramp capacitor 142 whose value is selectable by the operator for different sweep durations corresponding to different transmitter PRF's. Q24 is a lock-up for Q23 until the capacitor is charged. The collector of Q23 is connected through line 143 to Q25 and Q26 which form a cascade emitter follower including emitter resistors 144, 145. As capacitor 142 charges, the potential of line 143 rises. The potential at point 146 likewise rises and acts through capacitor 147 to turn on Q24. This keeps Q23 on until the capacitor is completely charged, whereupon Q24 turns off and Q23 turns off. The charging takes place very quickly.

A constant current discharge circuit for capacitor 142 comprises Q27 and Q28, the rate of discharge being adjustable by variable resistor 148, hence adjusting the sweep time duration. Transistors Q29 and potentiometer 149 provide drift control to eliminate temperature drift.

Figure 7:
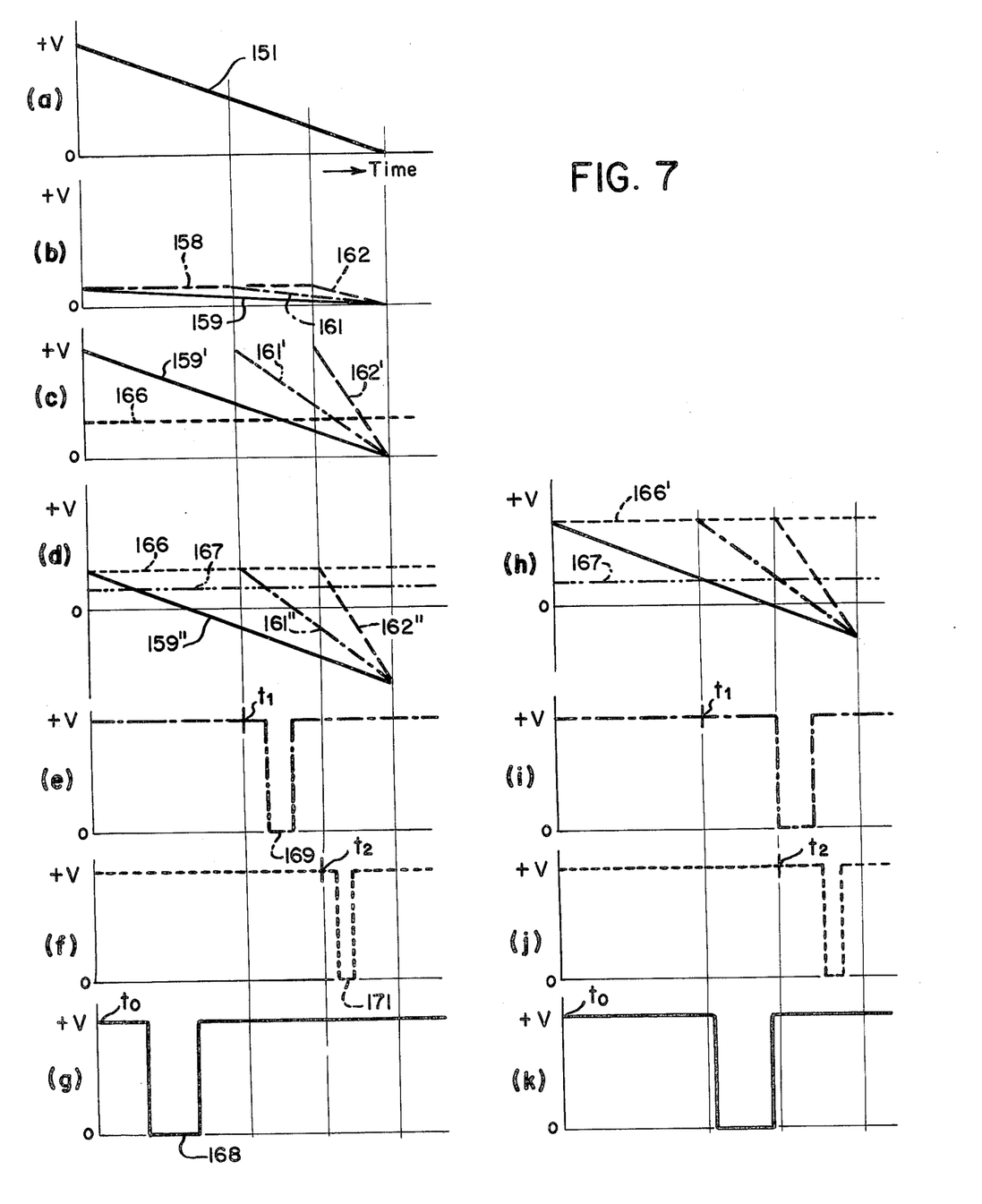
FIG. 7 shows explanatory waveforms for FIG. 6.

Overall, ramps of predetermined amplitude and duration are produced at point 146, as shown at 151 in FIG. 7 (and FIG. 4). Potentiometer 152 provides a variable attenuator for selecting a desired portion of the ramp amplitude. The selected portion in line 153 is supplied through diode 154 to point 155 which is connected to +V through variable resistor 156. Oppositely poled transistors Q30 and Q31 provide a limiter for limiting the voltage at point 155 to a maximum value and, with Q32, produce a sweep at point 157 of predetermined amplitude and adjustable delay with respect to the initial ramp 151.

Transistors Q30, Q31 and Q32 are initially on, yielding a positive voltage at point 155 as set by variable resistor 156. If the ramp voltage in line 153 exceeds the voltage at point 155, diode 154 is back biased and the voltage at 157 remains unchanged. As the ramp voltage in line 153 drops below the initial voltage at 155, diode 154 conducts and point 155 drops with the decreasing ramp voltage. This produces the desired sweep at point 157.

The operation is illustrated in FIG. 7. In (a), the initial ramp at point 146 is shown at 151. In (b), line 158 illustrates the initial voltage at point 155. Full line 159 represents a low setting of potentiometer 152 where the initial value of the attenuated ramp is equal to the limit level 158. Accordingly, as shown in (c), a full length undelayed sweep 159' is produced at 157. Dot-dash line 161 corresponds to a mid-position setting of potentiometer 152 wherein the first half of the attenuated ramp is limited, and only the second half produces the sweep. The corresponding expanded sweep 161' is produced at 157. Dash line 162 corresponds to a higher setting wherein the last one-quarter of the ramp produces a further expanded sweep shown at 162'.

An adjustable portion of the sweep is supplied to sweep output line 163 and thence to the horizontal scope amplifier 48 of FIG. 2. For the upper traces of FIG. 1 commonly full length undelayed sweeps will be employed, so that the complete video signal including transmitted pulse can be observed. However, the sweep can be expanded if desired to suit operating conditions.

As further explained in U.S. Pat. No. 3,972,228, the sweeps are supplied to a gate generator 49 so that gates of adjustable position and width may be produced. Detailed circuits are given in the patent and are not repeated here. Overall, an adjustable clamping level is selected to which the initial points of the sweeps are clamped, as shown at 166 in FIG. 7(d). This is the "Gate Pos." control. A second level 167 is adjustably selected by the "Gate Width" control. The gate pulse starts when the sweep passes line 167 and stops when it passes the reference line 0, commonly ground potential. With the levels 166 and 167 as shown, gate pulses 168, 169 or 171 will be produced, depending on whether sweep 159', 161' or 162' is being employed. On the CRT display, the observed lengths of the sweeps will be the same since the sweep amplitudes are the same. The initiations of the gates have the same proportions to the initiations of the sweeps ($t_o$, $t_1$ and $t_2$) as the sweep durations, so that the gates have the same observed positions on the CRT for different sweep expansions.

By changing the level of 166 as shown at 166' in (h), while leaving level 167 unchanged, the gate position along the sweep may be changed without changing its width. The resultant gates are shown in (i), (j) and (k) for sweeps of different expansion.

The gates shown in FIG. 7 are negative going. In the present application, positive going gates are desired. The gates are inverted and supplied to output line 122 and thence to FIG. 5 for display and control of signals to the theshold comparator for the upper traces.

Figure 6A:
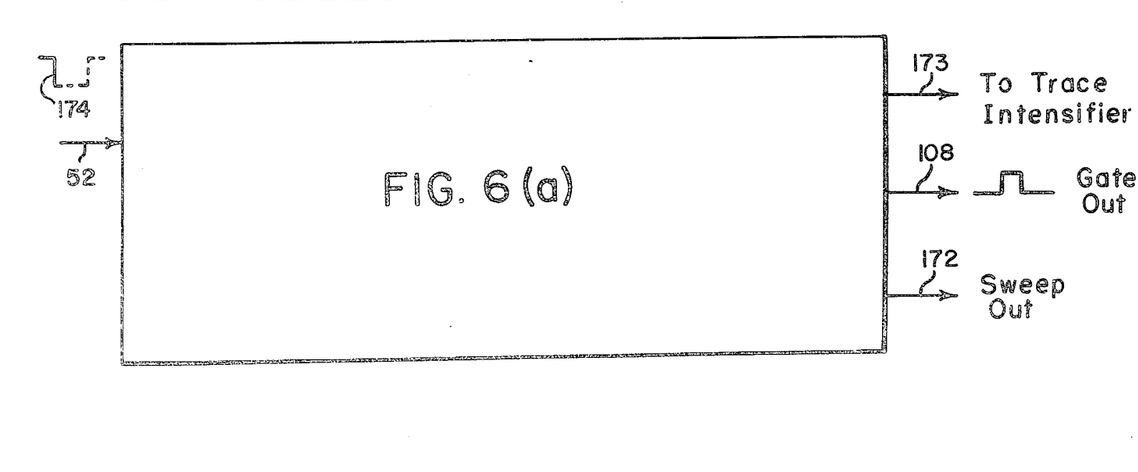

FIG. 6(a) is the sweep and gate generator for the lower traces. The internal circuits are the same as in FIG. 6, so that only a box is shown with corresponding inputs and outputs. Trigger pulse 174 from line 52 of FIG. 5 initiates the ramp when the pulse goes negative and the resultant sweep, further delayed or not as desired, appears in output line 172 and is supplied to the horizontal scope amplifier 48 of FIG. 2. The signal gate output in line 108 is supplied to FIG. 5 and functions as already described.

In the present embodiment the portions of the upper traces which are displayed on the lower traces are intensified. To this end, a sweep output from line 173 is supplied to the Z-axis amplifier 58 of FIG. 2. As seen in FIG. 6, the sweep at the output of Q31 is supplied through a diode to line 173'. Line 173' is not actually used, but the corresponding line in FIG. 6(a) is used. The sweep is sufficiently amplified and limited in 58 to intensify the CRT beam for the duration of the sweep.

In FIG. 1, the interface echo signal 13' on the lower traces is shown dotted, since its exact shape will depend on its amplitude as illustrated at 13 on the upper traces, and the height setting of the interface gate 17. When noise levels permit low gate settings, more of the interface echo will be visible on the lower traces.

As before mentioned, with a high PRF of the transmitted pulses, extraneous or spurious echoes may be produced by one pulse which are received after the next pulse is transmitted. Such spurious echoes may be displayed on subsequent sweeps and be interpreted as significant echoes. The test PRF may be reduced so that all echoes die out before a second pulse is transmitted. However, this increases the test time.

To enable the operator to distinguish spurious from significant echoes, echo check means are provided which temporarily changes the PRF of the transmitted pulses to a sub-multiple of the PRF being used for testing. As shown in FIG. 2, a pushbutton switch 180 supplies an appropriate blocking wave from generators 38 to the transmitter pulse generator 33 to eliminate selected pulses. By eliminating alternate pulses, the check PRF will be one-half the test PRF. More pulses may be eliminated to yield a still lower check PRF, and advantageously the check PRF is an even sub-multiple of the test PRF, for example, one-half, one-quarter, etc.

A specific arrangement is shown in FIG. 3. Transistor Q33 is connected across the input to Q2, with its emitter grounded and its collector connected to the base of Q2. The base of Q33 is connected through resistor 182 to one contact of pushbutton switch 180, and the other contact is connected to line 71. Waveform d of FIG. 4 appears in line 71. With the pushbutton switch open, Q33 is ineffective and pulse 183 in waveform a turns Q2 off at count 18 and on at count 20. Transmitter pulse 184 is produced at count 20 when Q2 goes on. Wave d is high from count 18 to count 38 and, with the pushbutton switch closed, turns on Q33 and maintains Q2 off until count 38, thereby eliminating transmitter pulse 184. At count 18, Q33 is turned off and allows pulse 185 in a to produce transmitter pulse 186 in b in normal manner. The operation continues and hence alternate transmitter pulses are eliminated, yielding a PRF as shown at j in FIG. 4 which is one-half the PRF of b.

As will be recognized, this change in PRF to a sub-multiple does not change wave $\overline{a}$ in line 68 of FIG. 3, which controls the sweeps from sweep generator 47 for the upper traces, as shown in FIGS. 2 and 6. Thus the sweeps are unchanged when the pushbutton switch is closed. As explained above, echoes in the upper traces are displayed every fourth sweep. Echoes arriving less than 20 counts after a pulse transmission will continue to be displayed at either PRF. However, echoes arriving between 20–40 counts will be displayed at the higher test PRF but not at the one-half check PRF. Thus spurious echoes in this range may readily be detected by momentarily actuating the pushbutton. If spurious echoes of sufficient amplitude occur in the range of 20–80 counts after a pulse transmission, they may be eliminated from the display by using a one-quarter check PRF. A still lower check PRF may be employed if necessary.

It is particularly important to check for a spurious echo within the interface gate of the upper traces, since this could cause erroneous triggering of the lower sweeps. If, upon checking, a true interface echo is within the interface gate, the checking will then reveal spurious echoes within the flaw gate of the lower traces.

If desired, the check circuit can be arranged to block alternate sweeps occurring between the sweeps which correspond to the non-eliminated pulses. This will eliminate the display of the gates, but may further assure that spurious echoes will not be displayed during the check period.

For proper operation of the check circuit, it is important that very stable PRF's be generated under both normal and check conditions. Otherwise the locations of the displayed echoes may shift and render the check operation ineffective. In the present embodiment such stability is assured by the use of the sine wave oscillator, square wave generator, and counters as described in connection with FIG. 3.

The invention has been described in connection with a specfic embodiment thereof, and detailed circuits have been given. It will be understood that certain features may be employed and others omitted, if desired, and the detailed circuitry changed as meets the needs of a particular application or the judgment of the designer.

I claim:

1. Ultrasonic non-destructive pulse testing apparatus which comprises (a) pulse generator and transducer means for applying ultrasonic pulses to an object to be tested, (b) means for receiving interface signals from an object under test and flaw signals corresponding to variations or defects in the object, (c) cathode-ray tube means for displaying received signals,
(d) first and second sweep generators for supplying sweeps to said cathode-ray tube means,
(e) an adjustable interface gate generator synchronized with said first sweep generator for producing an interface signal gate at a selectable position along the sweeps produced thereby,
(f) an adjustable threshold circuit supplied with received signals and with said interface signal gate for producing trigger signals when received signals within the gate exceed the threshold level thereof,
(g) means connected with said threshold circuit for producing from said interface signal gate a display interface signal gate having an amplitude substantially equal to the minimum amplitude of received signals as displayed which will actuate the threshold circuit to produce trigger signals,
(h) means for displaying said display interface signal gate and received signals during different sweeps from the first sweep generator and having coinciding baselines,
(i) means for utilizing said trigger signals to control the initiation of sweeps produced by said second sweep generator,
(j) a flaw signal gate generator synchronized with the second sweep generator for producing a flaw signal gate,
(k) and an adjustable flaw threshold circuit supplied with received signals and with the flaw signal gate for producing output signals when received signals within the flaw gate exceed an adjustable threshold level.

2. Apparatus according to claim 1 in which said flaw signal gate generator is adjustable to produce the flaw signal gate at a selectable position along the sweeps produced by the second sweep generator, and including means connected with the flaw threshold circuit for producing from the flaw signal gate a display flaw signal gate having an amplitude substantially equal to the minimum amplitude of received signals as displayed which will actuate the theshold circuit to produce said output signals, and means for displaying said display flaw signal gate and received signals during different sweeps from the second sweep generator and having coinciding baselines, the baselines of sweeps from the second sweep generator being displaced from the baselines of the sweeps from the first sweep generator as displayed on said cathode-ray tube means.

3. Apparatus according to claim 1 in which said interface gate generator is adjustable to change the width of the interface signal gate.

4. Apparatus according to claim 1 in which received signals and interface signal gate are continually displayed on predetermined sweeps from the first sweep generator and received signals and flaw signal gate are continually displayed on predetermined sweeps from the second sweep generator, the display of sweeps from the first generator being displaced from the display of sweeps from the second generator.

5. Apparatus according to claim 4 including means responsive to sweeps from the second sweep generator for brightening the corresponding portions of sweeps from the first sweep generator displayed by said cathode-ray tube means.

6. Apparatus according to claim 4 in which said first sweep generator and the interface gate generator produce a sweep and a gate respectively upon the occurrence of each transmitted pulse, and said second sweep generator and the flaw signal gate generator produce a sweep and a gate respectively upon the occurrence of each of said trigger signals, and including means for blocking from the said cathode-ray tube means the respective sweeps and gates and the received signals during other than said predetermined sweeps during which the received signals and gates are respectively displayed.

7. Apparatus according to claim 1 in which said pulse generator supplies transmitter pulses to said transducer means at a predetermined PRF and said first sweep generator is synchronized with said transmitter pulses, and including echo checking means for eliminating predetermined transmitter pulses to yield a PRF which is a sub-multiple of said predetermined PRF while maintaining unchanged the slope of the sweeps from said first sweep generator and the time occurrence of the sweeps with respect to the non-eliminated pulses.

8. Apparatus according to claim 7 in which said sub-multiple is an even sub-multiple of said predetermined PRF.

* * * * *